United States Patent
Suwald

(10) Patent No.: US 9,880,523 B2
(45) Date of Patent: Jan. 30, 2018

(54) POWERLESS TIME REFERENCE

(71) Applicant: NXP B.V., Eindhoven (NL)

(72) Inventor: Thomas Suwald, Hamburg (DE)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 14/305,939

(22) Filed: Jun. 16, 2014

(65) Prior Publication Data
US 2015/0003213 A1    Jan. 1, 2015

(30) Foreign Application Priority Data

Jun. 27, 2013 (EP) ..................................... 13174164

(51) Int. Cl.
| | |
|---|---|
| G04F 13/00 | (2006.01) |
| G06K 19/00 | (2006.01) |
| G04F 13/04 | (2006.01) |
| G04F 1/02 | (2006.01) |
| G04F 10/00 | (2006.01) |
| G04F 10/10 | (2006.01) |
| G01N 17/00 | (2006.01) |

(52) U.S. Cl.
CPC ................ *G04F 13/00* (2013.01); *G04F 1/02* (2013.01); *G04F 10/00* (2013.01); *G04F 10/10* (2013.01); *G04F 13/04* (2013.01); *G06K 19/00* (2013.01); *G01N 17/00* (2013.01)

(58) Field of Classification Search
CPC .......... G04F 10/00; G04F 10/10; G04F 13/00; G04F 13/02; G04F 13/04
USPC ................... 116/206; 368/114, 327
See application file for complete search history.

(56) References Cited

U.S. PATENT DOCUMENTS

| | | | | |
|---|---|---|---|---|
| 3,259,461 A | * | 7/1966 | Griffin, Jr. ............. | G01N 17/02 324/700 |
| 3,768,976 A | * | 10/1973 | Hu ........................... | G01K 3/04 116/207 |

(Continued)

FOREIGN PATENT DOCUMENTS

| | | |
|---|---|---|
| CA | 156416 S | 3/2015 |
| DE | 10 2010 014 918 B3 | 6/2011 |
| WO | 2015/131225 A1 | 9/2015 |

OTHER PUBLICATIONS

Kim, N. et al. "A Correlation Study Between Barrier Film Performance and Shelf Lifetime of Encapsulated Organic Solar Cell", Elsevier B.V.—Solar Energy Materials and Solar Cells, vol. 1, pp. 140-146 (Jun. 2012).

(Continued)

*Primary Examiner* — Amy Cohen Johnson
*Assistant Examiner* — Daniel Wicklund

(57) ABSTRACT

According to an embodiment, a time reference device is provided. In the embodiment, the time reference device, includes a corrodible element, wherein a corrosion of the corrodible element advances with advancing time, and a sensor configured for providing a sensor signal, the sensor signal depending on a physical property of the corrodible element; wherein the physical property of the corrodible element changes with a corrosion of the corrodible element and the physical property of the corrodible element is at least one of an electrical property, a magnetic property, and an optical property. A barrier may be provided for defining a permeability for a corrosive substance to the corrodible element.

14 Claims, 6 Drawing Sheets

(56) References Cited

U.S. PATENT DOCUMENTS

| | | | | |
|---|---|---|---|---|
| 3,983,527 | A | * | 9/1976 | Ohsato ................. G01N 27/121 200/61.04 |
| 4,056,445 | A | | 11/1977 | Gauntt et al. |
| 4,629,330 | A | * | 12/1986 | Nichols .................... G01K 3/04 368/327 |
| 4,860,269 | A | * | 8/1989 | Hennings et al. ............ 368/107 |
| 4,929,090 | A | * | 5/1990 | Grahm ...................... G04F 1/00 368/114 |
| 5,760,644 | A | | 6/1998 | Lancaster et al. |
| 6,198,701 | B1 | * | 3/2001 | De Jonghe et al. .......... 368/327 |
| 6,383,451 | B1 | * | 5/2002 | Kim ....................... G01N 17/04 324/71.1 |
| 7,048,195 | B2 | | 5/2006 | Berstis |
| 7,362,663 | B2 | * | 4/2008 | Kagan ........................... 368/327 |
| 7,907,330 | B2 | | 3/2011 | Delamarche et al. |
| 7,977,729 | B2 | | 7/2011 | Watanabe et al. |
| 8,104,949 | B2 | * | 1/2012 | Robinson et al. ............. 368/89 |
| 8,183,045 | B2 | * | 5/2012 | Faran ................................ 436/1 |
| 8,267,576 | B2 | * | 9/2012 | Haarer et al. ................. 374/102 |
| D765,177 | S | | 8/2016 | Hewitt et al. |
| 2004/0177685 | A1 | * | 9/2004 | Yokura ................. G01N 27/225 73/335.04 |
| 2006/0048572 | A1 | * | 3/2006 | Isogai .................. G01N 27/223 73/335.04 |
| 2006/0125493 | A1 | * | 6/2006 | Subramanian ......... G01N 17/04 324/700 |
| 2008/0219102 | A1 | * | 9/2008 | Su ........................ G01N 31/229 368/89 |
| 2009/0010304 | A1 | * | 1/2009 | Skinner et al. ................ 374/102 |
| 2009/0058427 | A1 | | 3/2009 | Materer et al. |
| 2010/0149929 | A1 | * | 6/2010 | Braunberger ................. 368/223 |
| 2010/0192688 | A1 | * | 8/2010 | Humbert et al. .......... 73/335.03 |
| 2013/0069676 | A1 | | 3/2013 | Steinwandel et al. |
| 2014/0330726 | A1 | | 11/2014 | Ball et al. |

OTHER PUBLICATIONS

Watanabe, H. et al. "Integrated Batteryless Electron Timer", IEEE Trans. on Electron Devices, vol. 58, No. 3, pp. 792-797 (Mar. 2011).
Extended European Search Report for EP Patent Appln. No. 13174164.7 (Nov. 12, 2013).

* cited by examiner

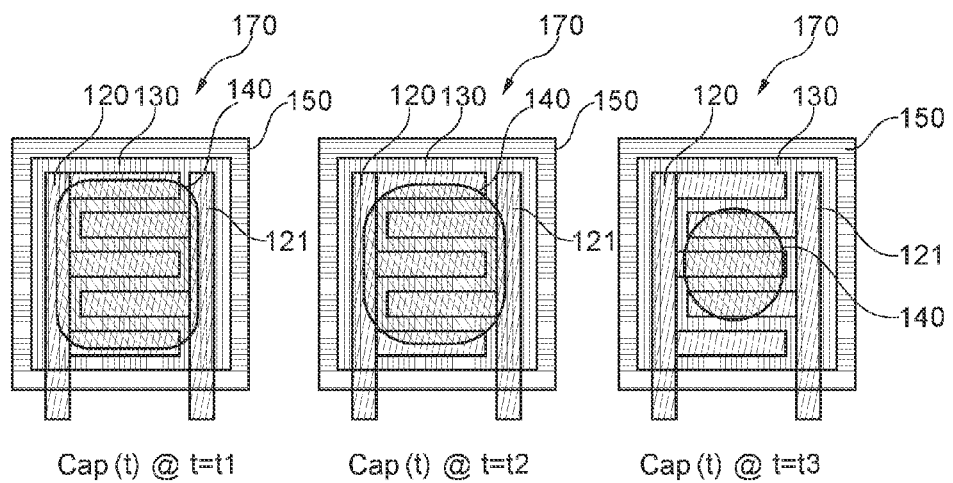
Fig. 4
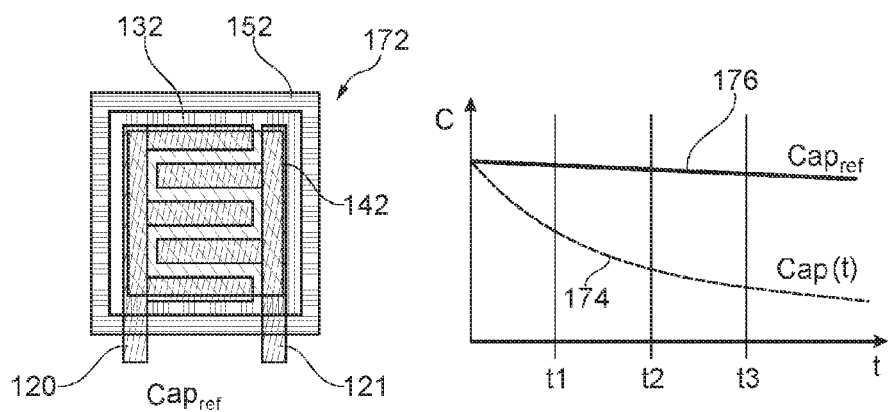
Fig. 5
Fig. 6

POWERLESS TIME REFERENCE

CROSS-REFERENCE TO RELATED APPLICATIONS

This application claims the priority under 35 U.S.C. § 119 of European patent application no. 13174164.7, filed on Jun. 27, 2013, the contents of which are incorporated by reference herein.

FIELD OF THE INVENTION

The present invention relates to the field of powerless time reference devices.

BACKGROUND OF THE INVENTION

U.S. Pat. No. 7,048,195 B2 relates to a method and system for expiring a device after a predetermined time period has elapsed. The device uses its own time cell so that the elapsed time is not altered through external time source. A charge storage element in the time cell includes floating gate field effect transistor, wherein the floating gate field effect transistor is configured within the time cell such that the floating gate field effect transistor turns on in response to applying power to the time cell after a predetermined time period has elapsed.

SUMMARY OF THE INVENTION

In view of the above described situation there exists a need for an improved technique that enables to provide a time reference system while substantially avoiding or at least reducing problems of known time cells.

This need may be met by the subject matter according to the independent claims. Advantageous embodiments of the herein disclosed subject matter are described by the dependent claims.

According to an embodiment of a first aspect of the herein disclosed subject matter there is provided a time reference device the time reference device comprising: A corrodible element, wherein a corrosion of the corrodible element advances with advancing time; a sensor configured for providing a sensor signal, the sensor signal depending on a physical property of the corrodible element; wherein the physical property of the corrodible element changes with a corrosion of the corrodible element; and wherein the physical property of the corrodible element is at least one of an electrical property, a magnetic property, and an optical property.

This aspect of the herein disclosed subject matter is based on the idea that the use of corrosive process as a basis for the time reference device may provide a simple and reliable device.

According to an embodiment no electrical power is required for the corrosion process to take place. This allows for determination of an elapsed time even if electrical power is not available or is only temporarily available. In this regard, it is noted that the fact that that the sensor is configured for providing a sensor signal does not necessarily mean that the sensor provides the sensor signal continuously. Rather, in an exemplary embodiment where the time reference device is included in a smartcard, the sensor is configured for providing the sensor signal upon request, e.g. upon powering the smartcard. According to an embodiment, the sensor signal is a signal the sensor provides if it is sampled by a suitable controller or a converter as disclosed herein. Further, the corrosion process is irreversible which may increase reliability of the time reference device. In particular, elapsed time cannot be reversed and the time reference device cannot be reset. The time reference device according to embodiments of the herein disclosed subject matter may be manufactured with the total thickness of less than 200 µm. This allows e.g. for an integration of the time reference device into smart cards, credit cards or the like.

According to an embodiment, the time reference device further comprises a barrier, the barrier providing a defined permeability for a corrosive substance through the barrier to the corrodible element, the corrosive substance generating the corrosion of the corrodible element. For example, the barrier may cover only a single surface of the time reference device. This may be suitable in the case of a smartcard wherein the time reference device is manufactured on the relatively thick substrate which is itself impermeable to the corrosive substance. According to an embodiment, the substrate is made of or at least comprises an electrically insulating material. According to an embodiment, the substrate is made of or comprises a metal layer, e.g. an aluminum layer. Metal as a substrate material has the advantage that it is not permeable for water vapor and oxygen. However, the sensor may require electrical insulation from the metal layer. According to an embodiment, the sensor (e.g. in the form of a capacitive or resistive sensor) is separated from the metal substrate by an electrical insulator.

According to a further embodiment the corrodible element is encapsulated by an insulating surface of or on the substrate and the barrier covering the corrodible element. The resulting encapsulation may include further parts of the time reference device, e.g. the sensor. According to other embodiments, the corrodible element and optionally further parts of the time reference device may be encapsulated in the barrier.

According to an embodiment, the time reference device further comprises a reference element; a further sensor configured for providing a reference signal, the reference signal depending on a physical property of the reference element; wherein the physical property of the reference element has a time dependence that is different from a time dependence of the physical property of the corrodible element; and wherein the physical property of the reference element is at least one of an electrical property, a magnetic property, and an optical property. For example, according to an embodiment the time dependence of the physical property of the reference element may be slower than the time dependence of the physical property of the corrodible element. This may be achieved e.g. by manufacturing the reference element from material which corrodes less than the corrodible element. In other words, according to an embodiment, the reference element is configured (e.g. shielded from ambient air) such that a corrosion of the reference element advances slower with time than the corrosion of the corrodible element. According to another embodiment the material of the reference element may be the same as of the corrodible element. In such a case, the different time dependence of the physical property of the corrodible element and the reference element may be generated by using a barrier for the reference element which is different from the barrier of the corrodible element. According to an embodiment, the time reference device further comprises a further barrier, the further barrier providing a defined permeability for the corrosive substance through the further harrier to the reference element; wherein for the corrosive substance the defined permeability provided by the further barrier for the reference element is lower than the defined permeability provided by the barrier for the corrodible element. For example, the barrier of the reference element may be of a different type or of e.g. a different thickness compared to the barrier of the corrodible element.

The sensor and the further sensor may be similar or identical. The greater the similarity of the sensor and the further sensor is, the easier may be the reduction of external effects, such as pressure effects or temperature effects. However, in other embodiments both sensors may be different.

According to an embodiment, the time reference device further comprises a converter, the converter being configured for providing a time signal, e.g. a machine readable time signal, in particular a machine readable representation of elapsed time, based on the sensor signal. According to an embodiment, the converter needs an external power source for providing the time signal on the basis of the sensor signal. According to an embodiment, the converter is configured to convert the level of corrosion into a machine readable representation of elapsed time. The term "elapsed time" generally represents a relative time, e.g. the time since the manufacturing of the time reference device or since an activation of the time reference device, e.g. by removal of a blocking barrier. Nonetheless the relative time may be used to generate an absolute time. Herein, a "machine readable time signal" may be any digital or analog time signal which can be read or received by electronic devices which are configured to read or receive the time signal. Further, a "machine readable representation of elapsed time" may be any digital or analog time signal which can be read or received by electronic devices which are configured to read or receive the representation of elapsed time.

According to an embodiment, the converter is configured for providing the (e.g. machine readable) time signal based on both, the sensor signal and the reference signal. In other words, the sensor signal as well as the reference signal are both used to generate the (e.g. machine readable) time signal. In this way for example pressure and/or temperature effects can be avoided or at least reduced. According to an embodiment, the time signal is generated based on difference of the sensor or signal and the reference signal.

According to an embodiment the time reference device further comprises: a synchronization unit capable of receiving a time synchronization signal provided by an external time reference; the converter being configured for providing the time signal by taking into account the time synchronization signal. In this way the converter may be configured for providing a more accurate absolute time signal. According to an embodiment, the time reference device comprises storage element for storing time reference information, e.g. an absolute time and the sensor signal and the reference signal at that time.

According to a further embodiment, the sensor comprises two measurement electrodes each of which is electrically connected or otherwise coupled to a terminal. According to an embodiment, the corrodible element is configured (e.g. located and of a suitable material) to increase the capacitive or inductive coupling between the two measurement electrodes. According to an embodiment, advancing corrosion of the corrodible element reduces the capacitive or inductive coupling between the two measurement electrodes. It should be understood that also three or more measurement electrodes may be provided.

According to an embodiment the sensor is a capacitor (herein also referred to as sensing capacitor) and a change in the physical property of the corrodible element (and hence a level of corrosion of the corrodible element) alters the capacitance of the capacitor. This embodiment has the advantage that precise methods for measuring the capacitance are known. For example, in an embodiment where the sensor is a capacitor, the capacitance of which changes with advancing corrosion of the corrodible element, the capacitor by its nature is configured to provide a sensor signal corresponding to the capacitance of the capacitor.

In cases where a capacitance is used as the sensor this capacitor is also referred to as sensing capacitor. In cases where a capacitance is used as the further sensor this capacitor is also referred to as reference capacitor.

According to an embodiment the corrodible element forms a first electrode of the capacitor; the capacitor comprises a counter electrode, the counter electrode and the first electrode forming the capacitor whose capacitance is altered by the change in the physical property of the corrodible element.

According to an embodiment, the capacitor comprises two measurement electrodes. The measurement electrodes may be formed by two counter electrodes of the capacitor. Measurement of the capacitance of the capacitor may include applying a voltage between the two measurement electrodes. According to a further embodiment, the capacitor comprises interdigitated electrodes, wherein the corrodible element is located in the vicinity of the interdigitated electrodes. According to an embodiment, the interdigitated electrodes and the corrodible element form series connected capacitors. Further, the interdigitated electrodes may be the measurement electrodes of the time reference device.

According to a further embodiment, the two measurement electrodes are located in a single plane. Hence, the capacitance of the measurement electrodes is mainly determined by the fringe field capacitance of the measurement electrodes (stray field capacitance). According to a further embodiment, the corrodible element is facing the measurement electrodes. According to an embodiment, the measurement electrodes are spaced from the corrodible element, e.g. by an insulator. According to an embodiment, the measurement electrodes and the corrodible element are configured such that advancing corrosion of the corrodible element alters the stray filed capacitance. According to an embodiment, the sensor is configured for providing a sensor signal that depends on the electrical conductivity of the corrodible element. For example, in an embodiment, where the corrodible element forms a capacitor plate of the sensor, the corrodible element represents indeed a capacitor plate in its non-corroded state and represents e.g. a dielectric layer in its fully corroded state. Hence, the sensor signal depends on the conductivity of the corrodible element (which changes from metal to insulator).

According to another embodiment, the physical property may be the electrical resistance of the corrodible element. Further, according to an embodiment the sensor is configured for measuring a resistance that depends on the corrosion state of the corrodible element, e.g. for measuring the electrical resistance of the corrodible element. The electrical resistance may be a suitable electrical property in particular for corrodible elements made. Examples of suitable corrodible elements include highohmic materials such as carbon and good conductors such as silver or copper. In particular in the latter case, the corrodible element may be provided by sputtering.

According to an embodiment, the sensor is configured for sensing magnetic property, e.g. a magnetization, wherein a change in the physical property/level of corrosion of the corrodible element alters the magnetic property sensed by the sensor. Sensors for magnetization are known in the art and may include e.g. magneto-resistive materials which change its resistance depending on an applied magnetic field. In such a case, the corrodible element may be a material layer having a permanent magnetic moment which diminishes with advancing corrosion of the corrodible element.

According to a further embodiment, the sensor is configured for sensing an optical property, e.g. a transmissibility, wherein a change in the physical property/level of corrosion of the corrodible element alters the optical property is sensed by the sensor. An optical property may be e.g. the transmissivity for a particular radiation. In such a case, the corrodible element may be a material layer which is optically transparent and which becomes opaque upon advancing corrosion of the corrodible element.

According to an embodiment, the corrodible element is a conductive element, in particular a metal element. For example, according to an embodiment the corrodible element is made of a reactive metal, e.g. of a metal of the first or second group of the periodic table of elements. According to an embodiment, the corrodible element is made of calcium.

According to an embodiment, the sensor comprises a first conductive layer and the corrodible element is formed by a second conductive layer; the first conductive layer being located parallel to the second conductive layer; and the first conductive layer being spaced apart from the conductive metal layer. For example, according to an embodiment the measurement electrodes are formed by the first conductive layer. According to an embodiment, the measurement electrodes are formed by the same, conductive layer.

Measurement of the capacitance of a capacitor is, according to an embodiment, performed by taking into account the charge that is transferred to an integration capacitor that may be configured to be electrically connected in series with the capacitor to be measured. In particular, according to an embodiment in a charge cycle the capacitor to be measured is first discharged and then connected to a fixed voltage and the integration capacitor is connected to ground. As a result, the capacitor to be measured is charged. Charging of the capacitor to be measured results in a current which in turn adds charge to the integration capacitor. Repeatedly performing the charge cycle results in an increasing charge on the integration capacitor and hence in an increased voltage across the integration capacitor. According to an embodiment, the number of charge cycles required to exceed a predetermined threshold voltage across the integration capacitor is defined as a measure for the capacitance. This sequence of charge cycles until the voltage across the integration capacitor exceeds the predetermined threshold voltage, is referred to herein as integration cycle.

According to an embodiment, the sensor signal is defined as the amount of charge accumulated in the capacitor to be measured if certain voltage is applied to it. However, it should be understood that generally, the sensor signal may depend on how the sensor is sampled and how the sampled signal is processed.

According to an embodiment, an individual integration capacitor is provided for each of the capacitor which forms the sensor for the corrodible element (sensing capacitor) and the capacitor which forms the sensor for the reference element (reference capacitor). According to a further embodiment, a common integration capacitor is provided for both, the capacitor which forms the sensor for the corrodible element and the capacitor which forms the sensor for the reference element. If a common integration capacitor is used, according to an embodiment the capacitances of the capacitor to be measured and of the reference capacitor are measured sequentially one after another.

According to an embodiment, the gain of the above described capacitance determination can be adjusted by the capacitance of the integration capacitor. According to a further embodiment, the gain of the above described capacitance determination is adjusted by multiple integration on the integration capacitor. This means, that the integration capacitor is discharged after the predetermined voltage threshold across the integration capacitor is exceeded but at least one further integration cycle is performed and the resulting counts (number of charge cycles required for exceeding the predetermined voltage threshold) are added. Hence, the final integration is split up into a charge integration via the integration capacitor and a numerical integration which may be performed by using a counter or calculator e.g. in a controller.

According to an embodiment a plurality of switches is provided for the capacitor to be measured and for the integration capacitor in order to perform the above mentioned actions and in particular the charge cycle and the integration cycle. To this end, the capacitor to be measured and the integration capacitor may be connected to either high voltage or ground or to each other e.g. to connect the capacitor to be measured and the integration capacitor in series, to discharge the capacitor to be measured, to charge the capacitor to be measured, to discharge the integration capacitor, etc. According to an embodiment a controller is provided for switching the plurality of switches in order to perform the above mentioned actions. The controller may be provided in hardware or software, or in hybrid form including hardware components and software components. Herein a software or software component may be any kind of computer program which is capable of running on a processor device.

According to an embodiment of a second aspect of the herein disclosed subject matter a device, for instance a wireless device e.g. in the form of a smartcard, is provided, the device comprising a time reference device according to the first aspect or an embodiment thereof.

According to embodiments of the second aspect, the method is adapted for providing the functionality of one or more of the aforementioned embodiments and/or for providing the functionality as required by one or more of the aforementioned embodiments, in particular of the embodiments of the first aspect.

According to an embodiment of a third aspect of the herein disclosed subject matter a method for providing a sensor signal indicative of an elapsed time is provided, the method comprising: providing a corrodible element, allowing the corrodible element to corrode with time; and providing the sensor signal by sensing a physical property of the corrodible element; wherein the physical property of the corrodible element changes with a corrosion of the corrodible element; and wherein the physical property of the corrodible element is at least one of an electrical property, a magnetic property, and an optical property.

According to embodiments of the third aspect, the method is adapted for providing the functionality of one or more of the aforementioned embodiments and/or for providing the functionality as required by one or more of the aforementioned embodiments, in particular of the embodiments of the first aspect and the second aspect.

As used herein, reference to a computer program is intended to be equivalent to a reference to a program element and/or a computer readable medium containing instructions for controlling a computer system to effect and/or coordinate the performance of the above described method.

The computer program may be implemented as computer readable instruction code by use of any suitable programming language, such as, for example, Assembler, JAVA, C, C++, and may be stored on a computer-readable medium (removable disk, volatile or non-volatile memory, embedded memory processor, etc.). The instruction code is operable to program a computer or any other programmable device to carry out the intended functions. The computer program may be available from a network, such as the World Wide Web, from which it may be downloaded.

Embodiments of the herein disclosed subject matter, in particular the functionality of the converter or the controller, may be realized by means of a computer program respectively software. However, the embodiments of the herein disclosed subject matter may also be realized by means of one or more specific electronic circuits respectively hardware. Furthermore, embodiments of the herein disclosed subject matter may also be realized in a hybrid form, i.e. in a combination of software modules and hardware modules.

In the above there have been described and in the following there will be described exemplary embodiments of the subject matter disclosed herein with reference to a time reference device, a smartcard, and a method for providing a sensor signal indicative of an elapsed time. It has to be pointed out that of course any combination of features relating to different aspects of the herein disclosed subject matter is also possible. In particular, some features have been or will be described with reference to apparatus type embodiments whereas other features have been or will be described with reference to method type embodiments. However, a person skilled in the art will gather from the above and the following description that, unless other notified, in addition to any combination of features belonging to one aspect also any combination of features relating to different aspects or embodiments, for example even a combinations of features of apparatus type embodiments and features of the method type embodiments is considered to be disclosed with this application.

The aspects and embodiments defined above and further aspects and embodiments of the herein disclosed subject matter are apparent from the examples to be described hereinafter and are explained with reference to the drawings, but to which the invention is not limited.

BRIEF DESCRIPTION OF THE DRAWINGS

FIG. 4 shows an elevated view of part of the measurement cell of FIG. 3 for different times.

FIG. 5 shows an elevated view of the reference cell of FIG. 3.

FIG. 6 shows schematically the time dependence of the capacitance of the measurement cell.

DETAILED DESCRIPTION

Figure 1:
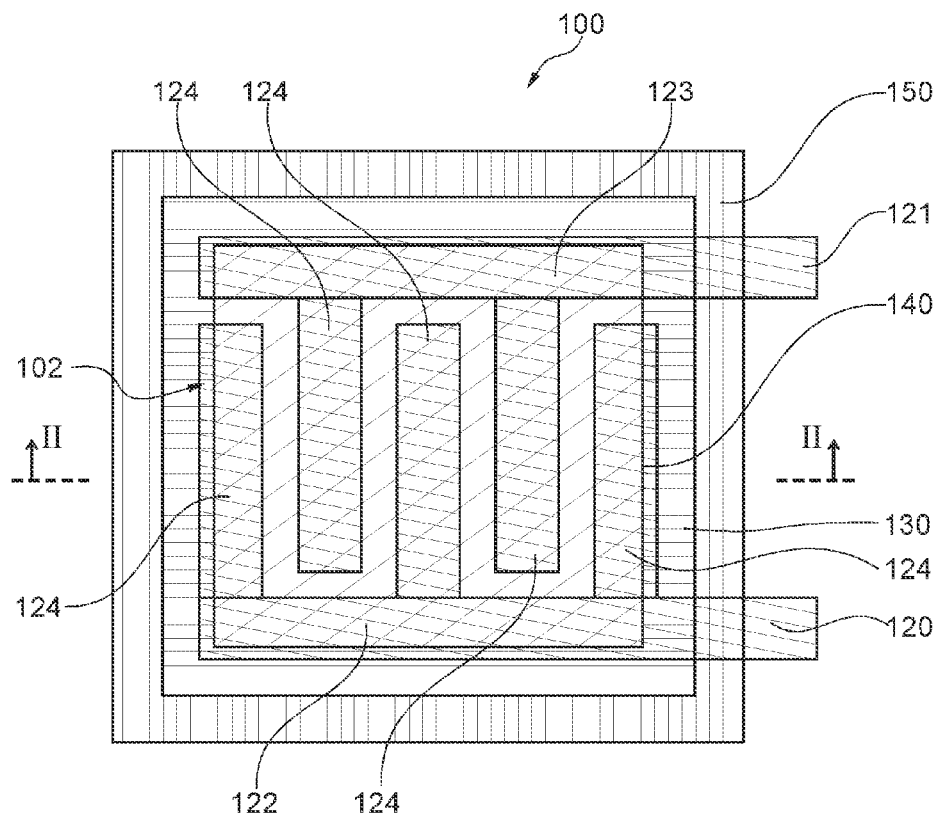
FIG. 1 shows a time reference device according to embodiments of the herein disclosed subject-matter.

The illustration in the drawings is schematic. It is noted that in different figures, similar or identical elements are provided with the same reference signs or with reference signs.

FIG. 1 shows a time reference device according to embodiments of the herein disclosed subject-matter.

The time reference device 100 comprises a corrodible element 140 in the form of a reactive electrode. A suitable material for the reactive electrode is calcium.

In accordance with an embodiment, the time reference device 100 comprises a sensor 102 configured for providing a sensor signal, wherein the sensor signal depends on a physical property of the corrodible element. In accordance with an embodiment, the physical property is an electrical property. Further in accordance with an embodiment, the corrodible element 140 is part of the sensor 102. For example, in an embodiment where the sensor 102 is a capacitor, the corrodible element 140 may form an electrode of the capacitor, as shown in FIG. 1. The sensor 102 further comprises first and second measurement electrodes 120, 121 (also referred to as first and second electrodes for short) which may be formed as interdigitated electrodes, as shown in FIG. 1. The measurement electrodes 120, 121 may be of copper, aluminum, gold, silver, carbon or other conducting or semiconducting materials or combinations thereof. In accordance with an embodiment, the interdigitated electrodes 120, 121 are formed by a metal layer, e.g. an aluminium layer on an electrical insulator 130 (in the following also referred to as "insulator" for short). A suitable material for the insulator 130 is e.g. aluminium oxide or parylene (provided by Para Tech). The insulator 130 may have a high dielectric constant (e.g. a high-k material). According to an embodiment, each of the interdigitated electrodes 120, 121 includes a base 122, 123 which is electrically connected to a plurality of conductive traces 124. According to an embodiment, the conductive traces 124 of the first electrode 120 are located parallel to the conductive traces 124 of the second electrode 121. According to an embodiment, the conductive traces 124 are straight conductive traces. According to a further embodiment, at least one conductive trace 124 of the second electrode 121 is located between two conductive traces 124 of the first electrode 120, as shown in FIG. 1.

The capacitor which is formed by the sensor 102 includes, in accordance with an embodiment, the first electrode 120, the second electrode 121, the corrodible element 140 as a corrodible electrode and the insulator 130 located between the electrodes 120, 121, 140. The capacitance of the capacitor is mainly determined by the fringe field capacitance of the interdigitated structure (stray field capacitance). According to an embodiment, the corrodible element 140 forms a floating electrode of the capacitor (sensor 102), i.e. the corrodible element 140 is electrically insulated in the time reference device 100. The electrically insulated corrodible element 140 in the form of a conductive layer on top of the measurement electrodes 120, 121 adds two series connected capacitors (conductive trace to corrodible element and corrodible element to the next conductive trace) in parallel to the capacitance of the two measurement electrodes 120, 121. Both series connected capacitors do mainly provide direct field capacitance. If the top layer corrodes away, the parallel capacitance reduces until the pure capacitance of the interdigitated structure (e.g. of the first and second electrodes 120, 121) is left.

The electrically insulated corrodible element 140 further has the advantage that a loss of conductive paths through the entire corrodible element does not affect the properties of the time reference device in a stepwise manner. Rather, volume properties of the corrodible element are sensed by the sensor 102 and in particular by the measurement electrodes 120, 121.

Generally according to an embodiment, the sensor 102 is configured for providing a sensor signal which depends on a volume physical property or at least a surface property of the corrodible element. In this way with advancing corrosion of the corrodible element a smooth sensor signal is provided. Instead of electrical properties, magnetic properties or optical properties of the corrodible element may be sensed by a respectively adapted sensor.

The time reference device 100 further comprises a barrier 150 which provides a defined permeability for a corrosive substance (not shown in FIG. 1). The barrier 150 is further discussed with regard to FIG. 2.

Figure 2:
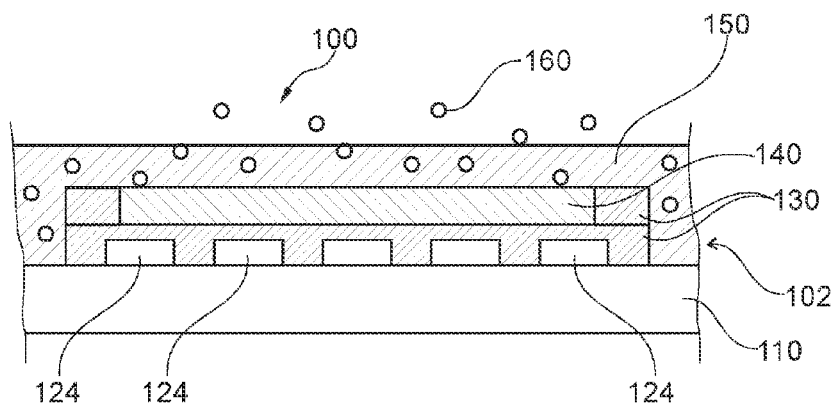
FIG. 2 shows a cross-sectional view of the time reference device of FIG. 1 along line II-II.

FIG. 2 shows a cross-sectional view of the time reference device 100 of FIG. 1 along line II-II.

According to an embodiment, the time reference device 100 is manufactured on a substrate 110, e.g. on an insulating surface of a substrate. According to a further embodiment, the substrate 110 may be of or may comprise any suitable insulating material, e.g. polyimide or polycarbonate In accordance with an embodiment, the time reference device 100 is manufactured as a separate element and is attached to the substrate afterwards. According to another embodiment, the time reference device 100 is manufactured on the substrate 110 by depositing respective layers of the time reference device 100 on the substrate 110. The manufacture of the time reference device 100 may involve any suitable known deposition processes and patterning processes.

Besides the elements already discussed with regard to FIG. 1 the description of which is not repeated here, FIG. 2 shows, in accordance with an embodiment, a barrier 150 and a corrosive substance 160 which may be e.g. water vapour or oxygen.

The barrier 150 provides a defined permeability for a corrosive substance 160 through the barrier 150 to the corrodible element 140. The corrosive substance 160 generates the corrosion of the corrodible element 140. The barrier 150 may be configured as an encapsulation of at least the corrodible element 140. If the substrate 110 has a sufficiently low permeability (in the order of the barrier), the barrier may only be provided over the corrodible element, but not between the corrodible element and the substrate. Hence, in accordance with an embodiment, the substrate 110 and the barrier 150 together form an encapsulation of the corrodible element 140, as shown in FIG. 2. According to an embodiment, the barrier 150 encapsulates the corrodible element 140 and optionally the sensor 102. According to an embodiment, the barrier 150 is in direct contact with the corrodible element, e.g. in a plane parallel to a surface of the substrate 110. According to a further embodiment, the corrodible element 140 is laterally spaced from the barrier 150, e.g. by an electrical insulator, e.g. by the electrically insulating material 130 which also isolates the conductive traces 124 of the measurement electrodes from the corrodible element 140.

As shown in FIG. 2, the corrosive substance 160 penetrates the barrier 150 and moves through the barrier 150 with a defined permeability which depends on the thickness and the material properties of the barrier 150. According to an embodiment, the barrier 150 is a moisture barrier. The moisture barrier may also act as an oxygen barrier with a low oxygen transmission rate (OTR).

Figure 3:
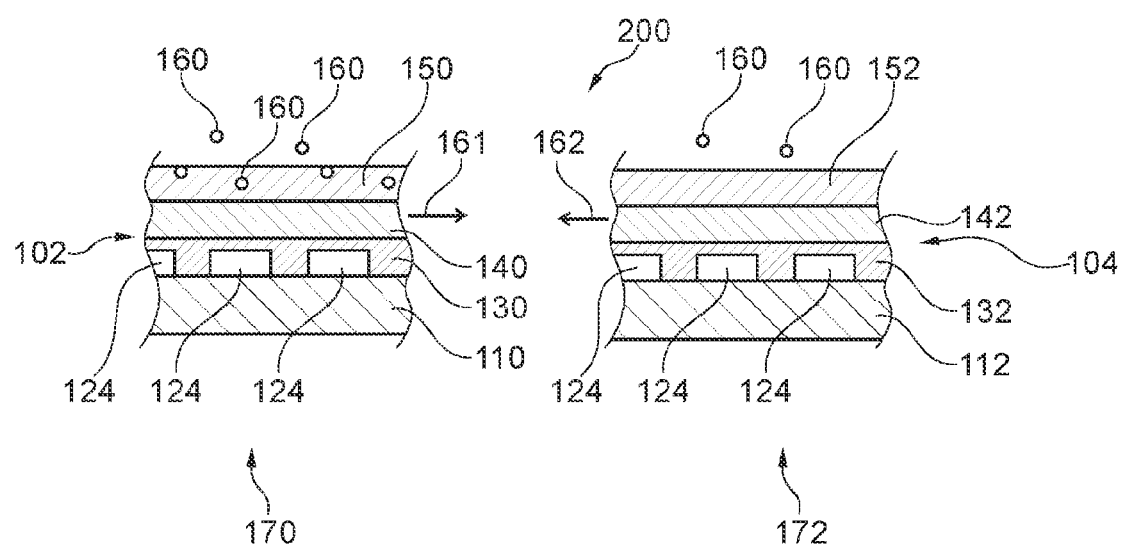
FIG. 3 shows part of a further time reference device according to embodiments of the herein disclosed subject-matter.

FIG. 3 shows part of a further time reference device according to embodiments of the herein disclosed subject-matter.

The time reference device 200 comprises a corrodible element 140 over an insulator 130 and first and second counter electrodes in the form of measurement electrodes, of which conductive traces 124 are shown in FIG. 3.

Further, the time reference device 200 comprises a reference element 142 which is located over an insulator 132 and first and second electrodes of which conductive traces 124 are shown in FIG. 3.

The corrodible element 140 and its associated sensor 102, which may partly be formed by the corrodible element itself, and at least one measurement electrode (represented by the conductive traces 124 in FIG. 3) and a barrier 150 for the corrodible element 140 form part of a measurement cell 170 of the time reference device 200.

According to an embodiment, the time reference device 200 further comprises a reference cell 172 which includes a reference element 142 and a further sensor 104 configured for providing a reference signal, wherein the reference signal depends on a physical property of the reference element 142. For example, according to an embodiment, a further sensor 104 comprises the reference element 142 and at least one measurement electrode associated with the reference element 142, wherein the at least one measurement electrode of the reference cell 170 is represented by the conductive traces 124 in FIG. 3.

According to an embodiment, the reference cell 172 comprises a further barrier 152, the further barrier providing a defined permeability for the corrosive substance 160 through the further barrier 152 to the reference element 142. For the corrosive substance 160, the defined permeability provided by the further barrier 152 is different, e.g. lower than, the defined permeability provided by the barrier 150 for the corrodible element 140. This has the advantage that the corrodible element 140 and the reference element 142 may be formed of the same material, e.g. a single material layer. However, in this regard it is noted that according to an embodiment, the corrodible element 140 and the reference element 142 are electrically isolated from each other, e.g. by a gap in the layer which forms the corrodible element 140 and the reference element 142. Such a gap may be provided by known patterning techniques. In effect, due to the lower permeability of the further barrier, the corrosion of the corrodible element 140 is faster than the corrosion of the reference element 142, in accordance with an embodiment.

When sampled by a suitable converter or controller e.g. a converter according to one or more embodiments of the herein disclosed subject matter, the sensor 102 provides a sensor signal, schematically indicated at 161 and the further sensor 104 provides a reference signal, schematically indicated at 162 in FIG. 1.

According to an embodiment, the measurement cell 170 is provided on a first substrate 110 and the reference cell 172 is provided on a second substrate 112. The first substrate 110 and the second substrate 112 may be individual substrates. Preferably, the first substrate 110 and the second substrate 112 are part of a single common substrate.

The sensor 102 may be referred to as a first sensor and the further sensor may be referred to as a second sensor. It is noted that the particular first sensor 102 described with regard to FIG. 3 and in particular the measurement electrodes, conductive traces 124 of which are shown in FIG. 3, may be replaced by any other suitable sensor. The choice of the type of first sensor 102 may depend e.g. on the material of the corrodible element. For example, if the corrodible element 140 in FIG. 3 is replaced by a corrodible element which has a permanent magnetization, the measurement electrodes may be replaced by e.g. a magneto-resistive sensor which changes its electrical resistance with magnetic field. This would lead to a change in electrical resistance of the magneto-resistive, sensor if corrosion of the corrodible element and hence a reduction of its magnetic moment advances. Likewise, the second sensor 104 described with regard to FIG. 3 may be replaced by any other suitable type of sensor. According to an embodiment, the first sensor 102 and the second sensor 104 are of the same type.

FIG. 4 shows an elevated view of part of the measurement cell 170 of FIG. 3 for times t=t1, t=t2 and t=t3. FIG. 5 shows an elevated view of the reference cell 172 of FIG. 3. The features of the measurement cell 170 and of the reference cell 172 are denoted by the same reference signs, the description of which is not repeated here.

For advancing time t the corrodible element diminishes and in particular, since corrosion is more effective at the edges of the corrodible element 114, reduces in its size, as shown in FIG. 4 for times the t1, t2 and t3, wherein t1<t2<t3. As mentioned with regard to FIG. 3, the barrier layer 150 for the corrodible element 140 of the measurement cell 170 is different from the barrier layer 152 of the reference cell 172 and the comprises a lower permeability to water vapor and/or oxygen. Due to the different barrier layer 152, the corrodible element 142 of the reference cell 172 almost maintains its size and thickness.

FIG. 6 shows schematically the time dependence of the capacitance C of the measurement cell 170, indicated at 174 and the capacitance C of the reference cell 172 indicated at 176, over time t.

As time advances, water vapour, oxygen and/or other substances such as acids (e.g. hydrochloric acid) slowly pass through the barrier layer 150 and react with the corrodible element 140 (also referred to herein as corrosion electrode). As a consequence, the conductivity of the corrodible element 140 may change significantly because the reaction product of the material of the corrodible electrode and water vapour and/or oxygen may have a far lower conductivity or may even be an insulator. The lower conductivity of the corrodible element 140 which is in the vicinity of the measurement electrodes 120, 121 of the sensor 102 leads to a reduced capacitance of between the measurement electrodes 120, 121 and the corrodible element 140 and hence results in a reduced capacitance of the sensor 102 (sensor capacitor). This explains the decrease of the capacitance 174 of the measurement cell over time t. Since the further barrier 152 of the reference cell 172 provides a much lower permeability for water vapour and/or oxygen, the corrosion of the reference element 142 proceeds much slower compared to the corrodible element 140. This explains the low time dependence of the capacitance 176 of the reference cell 172 over time t.

In practice, the further barrier 152 may be provided by a very good moisture barrier applied to the reference sensor capacitor (sensor 104) and the barrier 150 may be provided by a somewhat worse barrier 150 applied to the measurement capacitor (sensor 102). In another embodiment, the same barrier layer material may be applied to the measurement cell 170 and the reference cell 172 but at different thicknesses where for example the sensor 102 for the corrodible element 140 may have a reduced thickness compared to the barrier layer 152 for the reference element 142.

According to an embodiment, the reference cell 172 may be used to cancel mode impacts that may be caused by environmental parameters or systematic errors. One of these parameters may be pressure. Temperature effects may be reduced but may not be completely cancelled due to the Arrhenius equation.

In the following, an exemplary way is described of how capacitances of the measurement cell 170 and, if present, the reference cell 172 may be measured. It should be understood, that of course any other suitable device or method for measuring capacitances may be employed.

Figure 7:
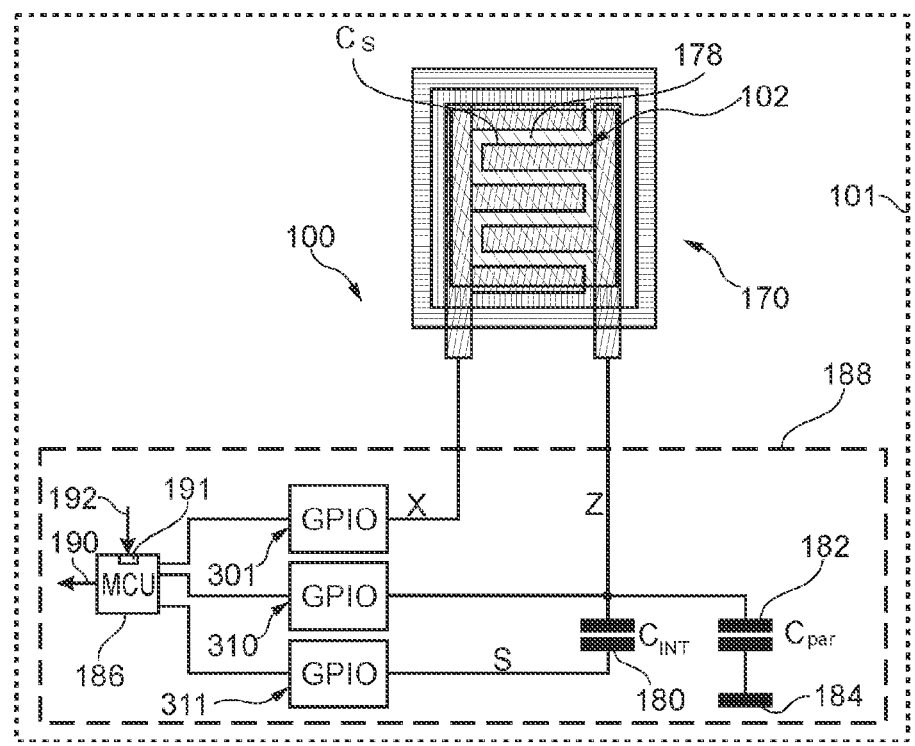
FIG. 7 shows a device in the form of a smartcard comprising a time reference device according to embodiments of the herein disclosed subject matter.

FIG. 7 shows a device in the form of a smartcard comprising a time reference device 100 according to embodiments of the herein disclosed subject matter.

According to an embodiment, the time reference device 100 is part of a smartcard 101. In accordance with an embodiment, the time reference device 100 comprises measurement cell 170 which may be configured according to embodiments disclosed herein and may be similar or identical to the measurement cell shown in FIG. 1. For this reason, the details of the measurement cell 170 are not repeated here. The measurement cell 170 includes, as the sensor 102, a capacitor 178 having a capacitance, indicated as $C_S$, the magnitude of which depends on the corrosion level of the corrodible element.

Measurement of the capacitance of the capacitor 178 is, according to an embodiment, performed by taking into account the charge that is transferred to an integration capacitor 180 having the capacitance $C_{INT}$. The integration capacitor is electrically connected in series with the capacitor 178 to be measured. In the real system, the parasitic capacitance 182, referred to as $C_{par}$ in FIG. 7, is present which represents the capacitances of wires, junction capacitances of transistor geometries, etc. The parasitic capacitance 182 appears as being connected to the integration capacitor 180 in parallel, e.g. to ground 184.

According to an embodiment in a charge cycle the capacitor 178 to be measured is first discharged by switching lines X and Z to the same potential. Thereafter, the capacitor 178 to be measured is connected to a fixed voltage and the integration capacitor 180 is connected to ground. As a result, the capacitor 178 to be measured is charged. Charging of the capacitor 178 to be measured results in a current flowing through the capacitor 178 and the integration capacitor 180. This current in turn adds charge to the integration capacitor 180. Repeatedly performing the charge cycle results in an increasing charge on the integration capacitor 180 and hence in an increased voltage across the integration capacitor 180. The number of charge cycles necessary to generate a predetermined voltage across the integration capacitor 180 corresponds to the capacitance $C_S$ of the capacitor 178 to be measured.

According to an embodiment, the sensor signal is defined as the change of charge being accumulated in the capacitor 178 to be measured if a certain voltage is applied to it, the change of charge corresponding to the capacitance $C_S$. It should be understood that the magnitude of the change of charge depends on the voltage applied to the capacitor 178 but is however related to the capacitance $C_S$ and hence to corrosion level of the corrodible element 140. Further, the change of charge corresponds to the integral of the charge current, generated by charging the capacitor 178, over time.

In accordance with an embodiment, a plurality of switches 301, 310, 311 is provided for the capacitor 178 to be measured and for the integration capacitor 180 in order to perform the above mentioned actions and in particular the to perform the charge cycle. To this end, the capacitor 178 to be measured and the integration capacitor 180 may be connected, by means of the switches 301, 310, 311, to either high voltage (not shown in FIG. 7) or ground 184, e.g. to charge the capacitor 178 to be measured, to discharge the integration capacitor 180, etc. According to an embodiment a controller 186 is provided for switching the plurality of switches 301, 310, 311 in order to perform the above mentioned actions. According to an embodiment, the controller is a microcontroller unit (MCU) configured to switch the switches 301, 310, 311. According to an embodiment, the switches 301, 310, 311 are a general-purpose input/output interfaces (GPIOs).

According to an embodiment, the integration capacitor 118, the parasitic capacitance 182, the switches 301, 310, 311 and the controller 186 form part of a converter 188 according to embodiments of the herein disclosed subject matter. According to an embodiment, the converter 188 provides a time signal 190 on the basis of the sensor signal. For example, according to an embodiment the controller 186 is configured for counting the charge cycles necessary to exceed the predetermined voltage level across the integration capacitor 180. According to a further embodiment, the controller 186 is further configured to calculate an elapsed time from the number of charge cycles, e.g. by using a lookup table which has been prepared for a particular capacitance value of the integration capacitor 180. The elapsed time herein corresponds to the time interval between start of the corrosion process and the actual time at which the capacitance $C_S$ is measured.

Depending on the actual implementation, the controller 186 may optionally take into account the capacitance of a reference cell, e.g. of the reference cell 172 described above, in order to provide the time signal 190. According to a further embodiment, the time reference device 100 comprises a synchronization unit 191 capable of receiving a time synchronization signal 192 which provides an external time reference. According to an embodiment, the converter 188 and, according to an embodiment shown in FIG. 7, the controller 186 is configured for providing the time signal 190 by taking into account the time synchronization signal 191. For example, the time synchronization signal 192 may be used by the controller 186 to synchronize the time calculated on the basis of the corrodible element 140 with the external time reference provided by the time synchronization signal 192. Since the corrosion process is not extremely precise it may be advantageous to synchronize the elapsed time whenever the time reference device (e.g. the smart card on which it is located) is connected to an authorized communication channel.

Figure 8:
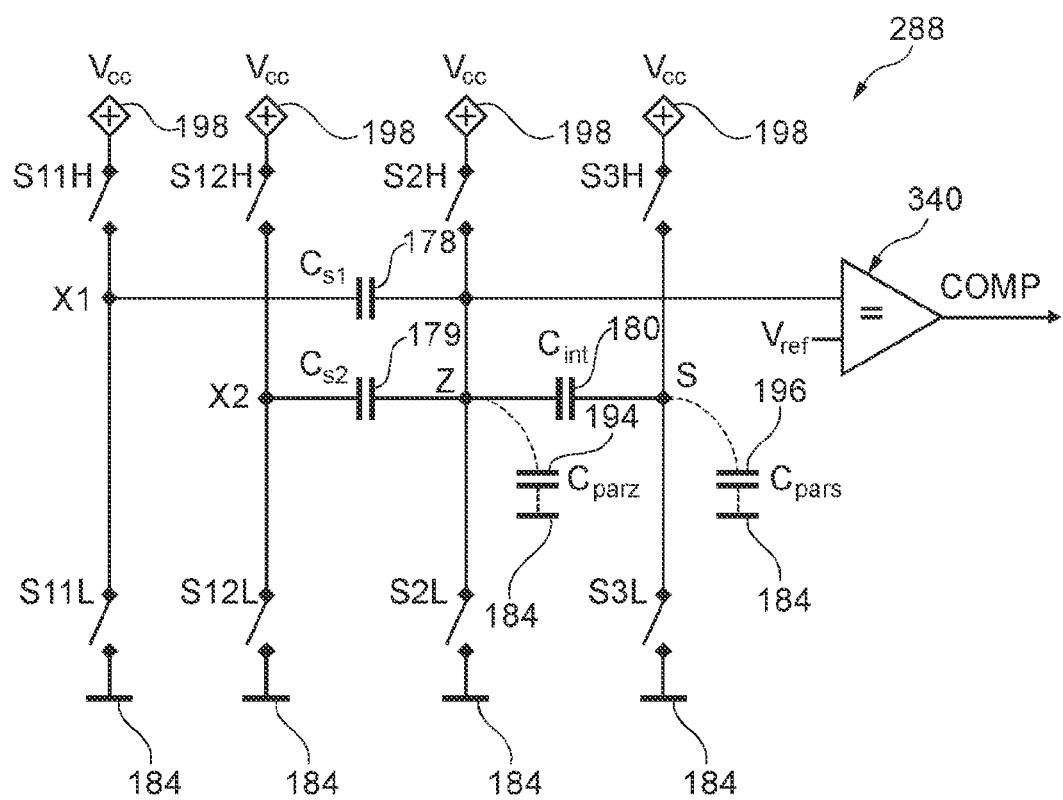
FIG. 8 shows part of a converter of a time reference device according to embodiments of the herein disclosed subject matter.

Nodes X, Z, S shown in FIG. 7 correspond to nodes X1 and X2, Z and S in FIG. 8 and are provided for easier comparison of both figures.

FIG. 8 shows part of a converter 288 of a time reference device according to embodiments of the herein disclosed subject matter.

In particular, the converter 288 includes a dual channel switched capacitor integrator according to embodiments of the herein disclosed subject matter. The converter 288 is provided for measuring the capacitance of the capacitor 178 of the measurement cell 170 and for measuring the capacitance of the capacitor 179 of the reference cell 172 with a single common integration capacitor. The capacitor 178 of the measurement cell 170, which is also referred to as sensing capacitor, has a capacitance denoted as CS1 in FIG. 8 and the capacitor 179 of the reference cell 172, which is also denoted as reference capacitor, has a capacitance denoted as CS2 in FIG. 8.

Measurement of the capacitance of the capacitors 178, 179 is, according to an embodiment, performed by taking into account the charge that is transferred to an integration capacitor 180 having the capacitance $C_{INT}$. The parasitic a capacitance of node Z is denoted as Cparz and the parasitic capacitance of node S is denoted as Cpars, corresponding to respective capacitors 194, 196.

According to an embodiment a plurality of switches S11H, S11L, S12H, S12L, S2H, S2L, S3H, S3L, is provided for the sensing capacitor 178, for the reference capacitor 179 and for the integration capacitor 180 in order to determine the capacitances of the sensing capacitor 178 and the reference capacitor 179 by performing charge cycles according to embodiments of the herein disclosed subject matter.

In the following, and an exemplary charge cycle for the sensing capacitor 178 is described. The charge cycle starts with all switches S11H, S11L, S12H, S12L, S2H, S2L, S3H, S3L open. In the charge cycle, first the capacitor to be measured, i.e. the sensing capacitor 178 in the described example, and the integration capacitor 180 are discharged. This may be performed by connecting the sensing capacitor 178 with both poles to the same potential, e.g. by closing the switches S11H and S2H or by closing the switches S11L and S2L. Afterwards, again all switches are opened. In a subsequent step the sensing capacitor 178 is connected to ground 184 via and in series with the integration capacitor 180 by closing the switch S3L which connects the integration capacitor 180 to ground 184. The floating terminal of the sensing capacitor 178 is now connected to a fixed voltage Vcc, indicated that 198, by closing switch resulting in a charge current through the series connected capacitors sensing capacitor 178 and integration capacitor 180). The charge current also adds charge to the integration capacitor 180. After the sensing capacitor 178 is fully charged (charge current is zero) switch S11H is opened while switch S31, is maintained closed, in order to provide the voltage across the integration capacitor 180 to a comparator 340. The comparator 340 determines whether the voltage across the integration capacitor 180 exceeds threshold voltage Vref. The comparator 340 may output a comparison signal COMP indicating whether the threshold voltage Vref is exceeded. Afterwards, the charge cycle is finished. The number of charge cycles required to exceed the threshold voltage is a measure of the capacitance of the sensing capacitor 178.

While the charge cycle for the sensing capacitor 178 has been described above, the charge cycle as well as the determination of the capacitance of the reference capacitor 179 may be performed in a similar way. According to an embodiment, the charge cycle for the reference capacitor 179 starts with all switches S11H, S11L, S12H, S12L, S2H, S2L, S3H, S3L open. In the charge cycle, first the capacitor to be measured, i.e. now the reference capacitor 179, and the integration capacitor 180 are discharged. This may be performed by connecting the reference capacitor 179 with both poles to the same potential, e.g. by closing the switch S12H and S2H or by closing the switches S12L and S2L. Afterwards, again all switches are opened. In a subsequent step the reference capacitor 179 is connected to ground 184 via and in series with the integration capacitor 180 by closing the switch S3L which connects the integration capacitor 180 to ground 184. The floating terminal of the reference capacitor 179 is now connected to a fixed voltage Vcc, indicated at 198, by closing switch S12H, resulting in a charge current through the series connected capacitors (reference capacitor 178 and integration capacitor 180). The charge current also adds charge to the integration capacitor 180. After the reference capacitor 179 is fully charged (charge current is zero) switch S12H is opened while switch S3L is maintained closed in order to provide the voltage across the integration capacitor to a comparator 340. The comparator 340 determines whether the voltage across the integration capacitor ISO exceeds threshold voltage Vref. Afterwards, the charge cycle is finished. The number of charge cycles required to exceed the threshold voltage is a measure of the capacitance of the reference capacitor 179.

Hence, following the above sequence, the capacitance of the sensing capacitor 178 as well as of the reference capacitor 179 can be determined with a single common integration capacitor 180. The plurality of switches S11H, S11L, S12H, S12L, S2H, S2L, S3H, S3L may be realized by any suitable means, e.g. by GPIOs described with regard to FIG. 7.

Figure 9:
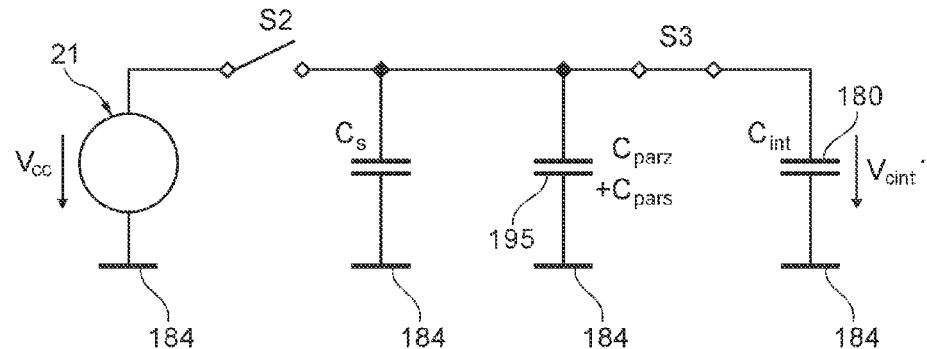
FIG. 9 and FIG. 10 illustrate the influence of parasitic capacitances on the charging and discharging of capacitors of FIG. 8.
Figure 10:
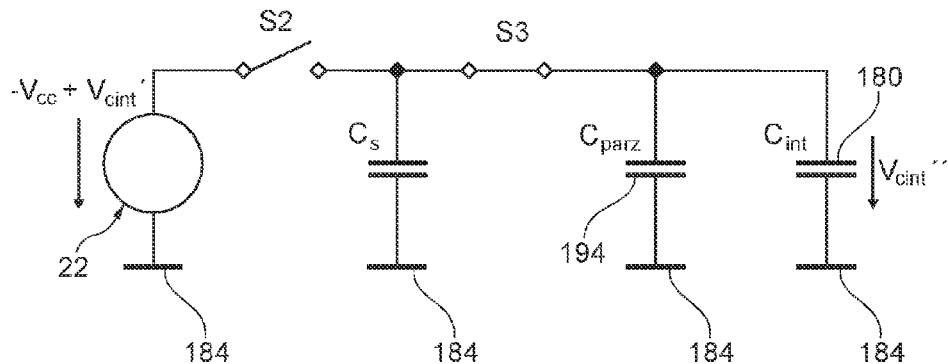

FIG. 9 and FIG. 10 illustrate the influence of parasitic capacitances on the charging and discharging of capacitors of FIG. 8. In particular, FIG. 9 illustrates the charging step and FIG. 10 illustrates the reverse (discharging) step.

With reference to FIG. 8, the parasitic capacitance of node S, Cpars (represented by parasitic capacitor 196), and the parasitic capacitance of node Z, Cparz (represented by parasitic capacitor 194), may be combined into a total parasitic capacitance Cpar=Cparz+Cpars for simplification in further considerations. Furthermore, the function will be described for one of the available two capacitors 178, 179 only, thus Cs will be used instead of Cs1 or Cs2 (see FIG. 8) respectively. Updating the charge on integration capacitor 180 (Cint) respectively the voltage across the integration capacitor 180 requires a charge step (FIG. 9) and a discharge step (FIG. 10) as set forth below.

The switched capacitor integrator of FIG. 8 is for simplification reasons transferred in the better visible form represented by FIG. 9. As can be seen the sensing capacitor 180 (capacitance Cs) and the combined parasitic node capacitance of node Z and node S, Cpar, are connected in parallel. They are used as a fly capacitor in a switched capacitor filter configuration. The function of the switches in FIG. 8 is thus transferred to the two switches S2 and S3. Bottom plate sampling by i.e. switch S3L in FIG. 8 has been transferred into top plate sampling by S3 in FIG. 9. Capacitor Cs is initially charge to Vcc by the virtual voltage source 21 through the closed S2 while S3 is kept open. The charge being moved during the charge step, when S2 is open and S3 is closed, into the integration capacitor Cint is in good approximation ΔQcint~(Vcc−Vcint)*(Cs+Cparz+Cpars). Vcint represents the voltage across the integration capacitor Chit at the beginning of a charge transport step, Vcint' (see FIG. 10) represents the voltage across the integration capacitor 180 (Cint) at the end of the charge transport step. Ground is indicated at 184 in FIGS. 9 and 10.

In preparation for the discharge step (FIG. 10) capacitor Cs is charged by the virtual voltage source 22 to the indicated voltage with S2 being closed and S3 being open. The charge being removed from the integration capacitor Cint during the discharge step, with S2 being open and S3 being closed, is according to FIG. 10 is in good approximation ΔQcint~Vcc*Cs. Discharging is hence independent of the voltage across the integration capacitor and can be regarded as a current related to the capacitance of Cs that discharges the integration capacitor. As can be seen from FIG. 8 the voltage across Cs changes polarity during this step. Vcint' represents the voltage across Cint at the beginning of the discharging step, Vcint" represents the voltage across Cint at the end of the discharging step.

In contrast, to a normal integrator with RC-behavior the voltage across Cint for the integrator shown in FIG. 8 (and FIGS. 9 and 10) does not necessarily approach Vcc. For this integrator, if added and removed charge ΔQint of the integration capacitor Cint is equal in size, the integration capacitor voltage will not increase any further. This voltage Vcint_max is in good approximation Vcint_max=Vcc*(Cparz+Cpars)/(Cs+Cparz+Cpars).

The combined parasitic capacitance Cpar should be as small as possible in order to achieve a good capacitance measurement resolution. Reference numbers 21 and 22 represent virtual voltage sources with the voltages as indicated. The virtual voltage sources arise from the consideration that a charged capacitor can be regarded as an uncharged capacitor connected in series to a virtual voltage source.

It is of an advantage for a circuit implementation if Vcint_max is selected to be close to Vcc/2, because in this case the comparator 340 in FIG. 8 can be replaced by a simple inverter or GPIO-input.

Having the measured capacitances, Cs1 and Cs2, the time interval is according to an embodiment defined by the relative capacitance variation:

$$(\Delta C(tn) - \Delta C(tn-1))/\Delta C(tn-1) \text{ with } \Delta C = Cref - C(t)$$

At the beginning of a time interval a target ΔC is defined that may correspond to certain duration. Upon next activation of the smartcard ΔC may be measured and may be compared against the predefined ΔC. If the predefined ΔC may be exceeded the end of the time interval is flagged to the smartcards security controller and related actions may be taken. It should be noted that, capacitances or quantities indicative thereof (e.g. the above mentioned counts) may be used for determining whether a certain time interval is exceeded. Instead of capacitances any quantity that is directly proportional to the capacitance may also be used.

The magnitude of the capacitance of the integration capacitor 180 determines the gain achieved with the converter 188, 288. The larger the number of charge cycles is, the lower is the relative error of the obtained number and the higher is the resolution of the capacitance determined. Hence, it is desirable to have a reasonable number of charge cycles. However, for a large capacitance of the capacitor to be measured, a relatively large integration capacitor would be needed. In order to obtain a reasonable resolution with a particular capacitance of the integration capacitor 180, the integration as described above may be executed multiple times and the number of charge cycles required to exceed the predefined threshold voltage Vref may be accumulated for each capacitor to be measured (sensing capacitor 178 and the reference capacitor 179), which is exemplarily described in the following.

Figure 11:
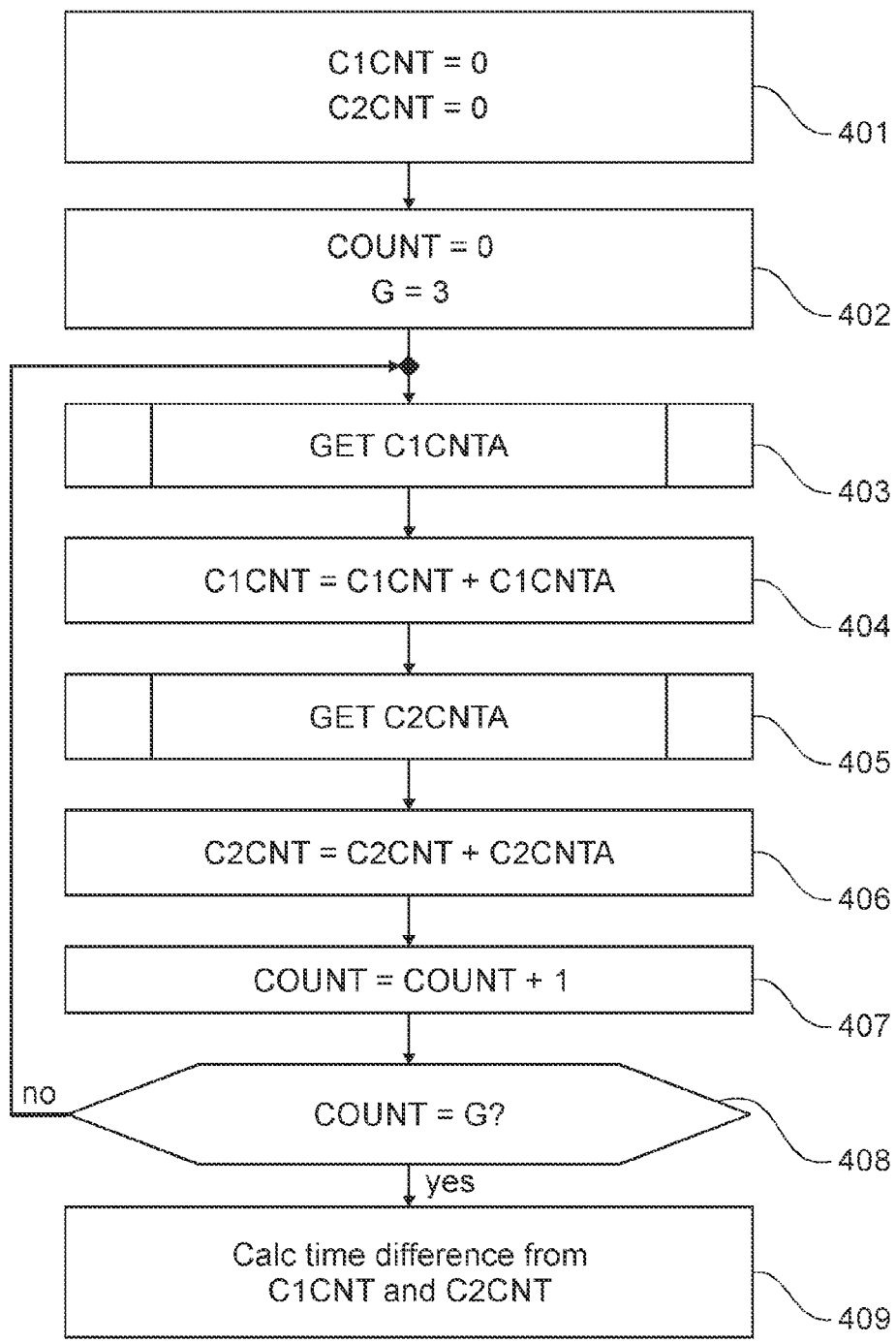
FIG. 11 shows a flow diagram for gain adjustment for the capacitance determination according to embodiments of the herein disclosed subject matter.

FIG. 11 shows a flow diagram for gain adjustment for the capacitance determination according to embodiments of the herein disclosed subject matter.

At 401 in FIG. 11, the value of an accumulation counter for sensing capacitor 178, C1CNT, is set to zero and the value of an accumulation counter for the reference capacitor 179, C2CNT, is set to zero.

At 402, a counter for the actual number of repetitions of the integration, COUNT, is set to zero and a maximum number of repetitions of the integration, G, is set to the desired value, "3" in the present case.

At 403, an actual value of the counter for the sensing capacitor 178, C1CNTA is retrieved.

At 404 the actual value of the counter for the sensing capacitor 178, C1CNTA is added to the accumulation counter value for the sensing capacitor 178, C1CNT. The result is taken as the new accumulation counter value for the sensing capacitor 178, C1CNT.

At 405, an actual value of the counter for the reference capacitor 179, C2CNTA is retrieved.

At 406 the actual value of the counter for the sensing capacitor 179, C2CNTA is added to the accumulation counter value for the sensing capacitor 179, C2CNT. The result is taken as the new accumulation counter value for the sensing capacitor 179, C1CNT.

At 407, the counter for the actual number of repetitions of the integration, COUNT, is incremented by 1.

At 408 a determination is made as to whether the actual number of repetitions of the integration, COUNT, is equal to the maximum number of repetitions of the integration, G. If the answer is "yes" then the method proceeds to 409. At 409, an elapsed time, i.e. a time difference between the point in time of manufacturing/activation of the time reference device and the time of measurement is calculated from the accumulation counter value for the sensing capacitor 179, C2CNT, and the accumulation counter value for the sensing capacitor 178, C1CNT. If the answer is "no", the method proceeds to 403, wherein 403 to 408 are repeated again.

In summary, according to an embodiment, a time reference device 100 is provided, which comprises a corrodible element 140, wherein a corrosion of the corrodible element 140 advances with advancing time, and a sensor 102 configured for providing a sensor signal, the sensor signal depending on a physical property of the corrodible element 140. The physical property of the corrodible element 140 changes with a corrosion of the corrodible element 140; and the physical property of the corrodible element 140 is at least one of an electrical property, a magnetic property, and an optical property. A barrier 150 may be provided for defining a permeability for a corrosive substance 160 to the corrodible element 140.

Applications of embodiments of the herein disclosed subject matter may include: Setting an expiry time of a cryptographic key; Controlling security parameter updates (e.g. requesting security update at an authorized terminal after expiry of a predetermined time); Stimulating an automated teller machine (ATM) to provide a marketing related message; Disabling a payment card for a predefined time interval; Enabling a payment card for a predefined time interval; Restricting the validity of an access time to predefined period.

The invention claimed is:

1. A time reference device comprising:
a corrodible element, wherein a corrosion of the corrodible element advances with advancing time;
wherein the corrosion of the corrodible element occurs without the requirement of electrical power; and
wherein the corrodible element forms a first electrode of a capacitor, the capacitor further comprising a counter electrode, the counter electrode and the first electrode forming the capacitor whose capacitance is altered by the corrosion of the corrodible element; and
a sensor configured for providing a sensor signal, the sensor adapted to sense the capacitance of the capacitor
a barrier, the barrier providing a defined permeability for a corrosive substance through the barrier to the corrodible element, the corrosive substance generating the corrosion of the corrodible element; and a further barrier, the further barrier providing a defined permeability for the corrosive substance through the further barrier to a reference element; wherein the defined permeability provided by the further barrier for the reference element is lower than the defined permeability provided by the barrier for the corrodible element.

2. The time reference device according to claim 1, further comprising:
a reference element;
a further sensor configured for providing a reference signal, the reference signal depending on a physical property of the reference element;
wherein the physical property of the reference element has a time dependence that is different from a time dependence of the corrosion of the corrodible element; and
wherein the physical property of the reference element is at least one of an electrical property, a magnetic property, and an optical property.

3. The time reference device according to the claim 2, the reference element being configured such that a corrosion of the reference element advances slower with time than the corrosion of the corrodible element.

4. The time reference device according to claim 2, further comprising:
a converter being configured for providing a time signal based on both, the sensor signal and the reference signal.

5. The time reference device according to claim 1, further comprising:
a converter, the converter being configured for providing a machine readable representation of elapsed time, based on the sensor signal.

6. The time reference device according to claim 5, further comprising:
a synchronization unit capable of receiving a time synchronization signal provided by an external time reference; and
the converter being configured for providing a time signal by taking into account the time synchronization signal.

7. The time reference device according to claim 1, the capacitor comprising interdigitated electrodes, wherein the corrodible element is located in the vicinity of the interdigitated electrodes and the corrodible element and the interdigitated electrodes form series connected capacitors.

8. The time reference device according to claim 1, wherein the corrodible element is a metal element.

9. The time reference device according to claim 1, wherein the sensor comprises a first conductive layer and the corrodible element is formed by a second conductive layer;
the first conductive layer being located parallel to the second conductive layer; and
the first conductive layer being spaced apart from the second conductive layer.

10. A device in the form of a smartcard, the device comprising a time reference device according to claim 1.

11. The time reference device of claim 1, wherein the reference element and the corrodible element are formed from the same material in a single metal layer.

12. A method for providing a sensor signal indicative of an elapsed time, the method comprising:

providing a corrodible element;

allowing the corrodible element to corrode with time;

wherein the corrosion of the corrodible element occurs without the requirement of electrical power;

wherein the corrodible element forms a first electrode of a capacitor, the capacitor further comprising a counter electrode, the counter electrode and the first electrode forming the capacitor whose capacitance is altered by the corrosion of the corrodible element; and providing a sensor signal by sensing the capacitance of the capacitor providing a barrier with a defined permeability for a corrosive substance, the corrosive substance generating the corrosion of the corrodible element; providing a further barrier with a defined permeability for the corrosive substance to a reference element; wherein the defined permeability of the corrosive substance through the further barrier to the reference element is lower than the defined permeability of the corrosive substance through the barrier to the corrodible element.

13. The time reference device of claim 1, wherein corrosion of the corrodible element is irreversible.

14. The time reference device of claim 1, wherein the corrodible element is configured to corrode due to the presence of at least one of moisture and oxygen.

* * * * *